US012758305B2

(12) United States Patent
Bonn

(10) Patent No.: US 12,758,305 B2
(45) Date of Patent: Oct. 13, 2026

(54) ELECTROSURGICAL BLADE ELECTRODE ADDING PRECISION DISSECTION PERFORMANCE AND TACTILE FEEDBACK

(71) Applicant: Covidien LP, Mansfield, MA (US)

(72) Inventor: Kenlyn Bonn, Lakewood, CO (US)

(73) Assignee: Covidien LP, Mansfield, MA (US)

( * ) Notice: Subject to any disclaimer, the term of this patent is extended or adjusted under 35 U.S.C. 154(b) by 1019 days.

(21) Appl. No.: 17/602,002

(22) PCT Filed: Apr. 16, 2020

(86) PCT No.: PCT/CN2020/085024

§ 371 (c)(1),
(2) Date: Oct. 7, 2021

(87) PCT Pub. No.: WO2020/211797

PCT Pub. Date: Oct. 22, 2020

(65) Prior Publication Data

US 2022/0151683 A1 May 19, 2022

Related U.S. Application Data

(60) Provisional application No. 62/835,070, filed on Apr. 17, 2019.

(51) Int. Cl.
*A61B 18/14* (2006.01)
*A61B 18/00* (2006.01)

(52) U.S. Cl.
CPC .. *A61B 18/148* (2013.01); *A61B 2018/00136* (2013.01); *A61B 2018/00309* (2013.01);
(Continued)

(58) Field of Classification Search
CPC ........ A61B 18/148; A61B 2018/00136; A61B 2018/00309; A61B 2018/00577;
(Continued)

(56) References Cited

U.S. PATENT DOCUMENTS 4,228,800 A 10/1980 Degler, Jr. et al.
7,824,398 B2 11/2010 Woloszko et al.
(Continued)

FOREIGN PATENT DOCUMENTS

CN 105286990 A 2/2016
CN 106137385 A 11/2016
(Continued)

OTHER PUBLICATIONS

International Search Report and Written Opinion of the International Searching Authority issued in corresponding application PCT/CN2020/085024 mailed Jul. 20, 2020 (9 pages).
(Continued)

*Primary Examiner* — Eun Hwa Kim
*Assistant Examiner* — Catherine Premraj
(74) *Attorney, Agent, or Firm* — Carter, DeLuca & Farrell, LLP

(57) ABSTRACT

An electrosurgical blade (900) configured to couple to an RF electrosurgical instrument (100). The electrosurgical blade (900) includes a proximal portion (900*a*) configured to couple to a blade receptacle (104) of an RF electrosurgical instrument (100), a coagulation section (920) extending distally from the proximal portion (900*a*), a blade edge (940) defined around a periphery of the electrosurgical blade (900), and a ramped surface (930) extending between the coagulation section (920) and the blade edge (940). The blade edge (940) includes a right-angled tip (944) and is defined by a first side (941) extending longitudinally, a second side (942) extending longitudinally and having a curved portion (942*c*), and a distal side (943) extending laterally.

20 Claims, 8 Drawing Sheets

(52) U.S. Cl.
CPC ............... *A61B 2018/00577* (2013.01); *A61B 2018/00589* (2013.01); *A61B 2018/00601* (2013.01); *A61B 2018/1495* (2013.01)

(58) Field of Classification Search
CPC ........... A61B 2018/00589; A61B 2018/00601; A61B 2018/1495
See application file for complete search history.

(56) References Cited

U.S. PATENT DOCUMENTS

| | | | |
|---|---|---|---|
| 2001/0020167 | A1 | 9/2001 | Woloszko et al. |
| 2003/0009164 | A1* | 1/2003 | Woloszko ............ A61B 18/149 606/49 |
| 2003/0130655 | A1 | 7/2003 | Woloszko et al. |
| 2006/0241587 | A1 | 10/2006 | Heim et al. |
| 2010/0016854 | A1 | 1/2010 | Carmel et al. |
| 2012/0215217 | A1 | 8/2012 | Horner et al. |
| 2018/0256243 | A1 | 9/2018 | Cosmescu |

FOREIGN PATENT DOCUMENTS

| | | | |
|---|---|---|---|
| CN | 107427324 | A | 12/2017 |
| WO | 2018081820 | A1 | 5/2018 |
| WO | 2018090044 | A1 | 5/2018 |

OTHER PUBLICATIONS

Partial European Search Report dated Dec. 13, 2022, issued in corresponding EP Appln. No. 20791161, 13 pages.

* cited by examiner

ELECTROSURGICAL BLADE ELECTRODE ADDING PRECISION DISSECTION PERFORMANCE AND TACTILE FEEDBACK

CROSS-REFERENCE TO RELATED APPLICATIONS

This application is a U.S. National Stage Application filed under 35 U.S.C. § 371 (a) of International Patent Application No. PCT/CN2020/085024, filed Apr. 16, 2020, which claims priority to and the benefit of, U.S. Provisional Application Ser. No. 62/835,070, entitled "ELECTROSURGICAL BLADE ELECTRODE ADDING PRECISION DISSECTION PERFORMANCE AND TACTILE FEEDBACK," filed on Apr. 17, 2019, the entire contents of which are incorporated by reference herein.

FIELD

The present disclosure relates to an electrosurgical electrode and, more particularly, to an electrosurgical blade electrode having an asymmetric configuration and insulative coating for precise dissection during an electrosurgical procedure.

BACKGROUND

Electrosurgical instruments have become widely used by surgeons in recent years. By and large, most electrosurgical instruments are hand-held instruments, e.g., an electrosurgical pencil, which transfer electrosurgical energy, e.g., radio-frequency (RF) electrosurgical energy, to a tissue site via an electrosurgical electrode. Typically, the electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical cutting and fulguration.

Typically, electrosurgical electrodes configured for electrosurgical use are subject to high temperatures at least where an electrosurgical arc emanates during the electrosurgical procedure, e.g., fulguration or coagulation. In some instances, the heat generated by the electrosurgical electrode during an electrosurgical procedure may cause proteins in bodily fluids and/or tissue to coagulate and adhere to the electrodes. To combat this adhering of bodily fluids and/or tissue to the electrosurgical electrodes, an insulative coating, e.g., a Teflon polymer, may be applied to the electrosurgical electrode.

Typical open electrode blades are symmetrical in design, are uniformly flat or have a slightly tapered cross section. These geometrical features enable the most common use for blade electrodes, blunt dissection and spot coagulation. However, the growing need for precision dissection capabilities and improved healing response (reduced thermal damage) on long skin incisions, has brought about a new family of blade electrodes that offer RF concentration features along the entire length of the blade. Two common features that enable precision dissection are either a sharp needle like electrode or a narrow cross section. Both designs have safety concerns in the operating rooms though. Specifically, the needle adds a sharp object that could perforate protective gloves and the RF sharp blades have no controlling feature to reduce the amount of the blade that can enter the dissection plane. When active, the blade can easily plunge into tissue with very little resistance (even less resistance than a surgical blade).

SUMMARY

The following aspects of electrosurgical instruments, and in particular, electrosurgical blade electrodes for electrosurgical instruments, incorporate features to enable fine precision dissection while still maintaining the coagulation capabilities of the blade electrodes. In particular, aspects of electrosurgical blade electrodes disclosed herein include structural features and properties that enable precision dissection of tissue, improving maneuverability of the blade electrode though tissue and improving safety by providing tactile features to the user or robotic system at set depths through tissue. Some aspects of electrosurgical blade electrode designs disclosed herein offer a significantly reduced section for precision on the edge of the blade, then two semi-circular cut outs that also provide the tactile feedback for detecting the depth of the electrode during tissue dissection. The reduced width of the cross section at this location improves the maneuverability of the blade and ultimately the instrument.

In an aspect, the present disclosure is directed to an electrosurgical blade configured to couple to an RF electrosurgical instrument. The electrosurgical blade includes a proximal portion configured to couple to a blade receptacle of an RF electrosurgical instrument, a first section extending distally from the proximal portion and having a first thickness, a second section extending distally from the first section and having a second thickness less than the first thickness thereby defining a first step between the first section and the second section, a third section extending distally from the second section and having a third thickness less than the second thickness thereby defining a second step between the second section and the third section, and a blade edge disposed along a peripheral edge of the third section.

The blade edge may be defined by a first side, a second side, and a third side, where the first side has a first length and the second side has a second length less than the first length.

In an aspect, the third section is configured to transmit a higher RF concentration than the second section to easily start a transection. Additionally or alternatively, the first section is coated to limit RF energy transmission from the first section relative to the remaining sections thereof. The second section may additionally or alternatively be coated to limit RF energy transmission from the second section.

In an aspect, at least one of the first section or the second section is configured to transmit RF energy therefrom only when provided a high voltage coagulation signal.

The second step is dimensioned and configured to provide a tactile feedback to a user during dissection. At least one of the first step or the second step may be a ramped surface or a non-ramped perpendicular surface.

In another aspect of the present disclosure, an RF electrosurgical instrument is provided. The RF electrosurgical instrument includes a blade receptacle and an electrosurgical blade operatively coupled thereto. The electrosurgical blade includes a proximal portion configured to couple to a blade receptacle of an RF electrosurgical instrument, a first section extending distally from the proximal portion and having a first thickness, a second section extending distally from the first section and having a second thickness less than the first thickness thereby defining a first step between the first section and the second section, a third section extending distally from the second section and having a third thickness less than the second thickness thereby defining a second step between the second section and the third section, and a blade edge disposed along a peripheral edge of the third section.

The blade edge may be defined by a first side, a second side, and a third side, where the first side has a first length and the second side has a second length less than the first length.

In an aspect, the third section is configured to transmit a higher RF concentration than the second section to easily start a transection. Additionally or alternatively, the first section is coated to limit RF energy transmission from the first section relative to the remaining sections thereof. The second section may additionally or alternatively be coated to limit RF energy transmission from the second section.

In an aspect, at least one of the first section or the second section is configured to transmit RF energy therefrom only when provided a high voltage coagulation signal.

The second step is dimensioned and configured to provide a tactile feedback to a user during dissection. At least one of the first step or the second step may be a ramped surface or a non-ramped perpendicular surface.

In yet another aspect of the present disclosure, an electrosurgical system is provided. The electrosurgical system includes an electrosurgical generator configured to generate RF electrosurgical energy and an RF electrosurgical instrument configured to couple to the electrosurgical generator and transmit RF electrosurgical energy to tissue. The RF electrosurgical instrument includes a blade receptacle and an electrosurgical blade operatively coupled thereto. The electrosurgical blade includes a proximal portion configured to couple to a blade receptacle of an RF electrosurgical instrument, a first section extending distally from the proximal portion and having a first thickness, a second section extending distally from the first section and having a second thickness less than the first thickness thereby defining a first step between the first section and the second section, a third section extending distally from the second section and having a third thickness less than the second thickness thereby defining a second step between the second section and the third section, and a blade edge disposed along a peripheral edge of the third section.

The blade edge may be defined by a first side, a second side, and a third side, where the first side has a first length and the second side has a second length less than the first length.

In an aspect, the third section is configured to transmit a higher RF concentration than the second section to easily start a transection. Additionally or alternatively, the first section is coated to limit RF energy transmission from the first section relative to the remaining sections thereof. The second section may additionally or alternatively be coated to limit RF energy transmission from the second section.

In an aspect, at least one of the first section or the second section is configured to transmit RF energy therefrom only when provided a high voltage coagulation signal.

The second step is dimensioned and configured to provide a tactile feedback to a user during dissection. At least one of the first step or the second step may be a ramped surface or a non-ramped perpendicular surface.

Traditional monopolar open blades utilize radiofrequency electrical energy to heat the tissue to achieve transection or hemostasis. The activation of RF power can cause inevitable sparking, which, although may assist in the hemostasis, can cause unintended thermal damage to the nearby tissue and critical structure and has a high risk of deflagration in the surgical environment. Especially in surgeries that are sensitive to thermal damage, surgeons have to be very careful when activating monopolar blades to prevent nerves and vessels from unintended damage. The disclosed blade configurations have less thermal spread and lower activation power to meet the needs of precise surgeries and lower the risk of potential damage to nearby tissue and critical structures. In particular, the present disclosure provides an asymmetric monopolar open blade with partial insulative coating for achieving minimal lateral thermal damage and smoke generation when activated to transect tissue. The disclosed blade includes a tip feature that enable surgeons to perform precise dissection and hemostasis while utilizing a lower power setting.

In accordance with another aspect, the present disclosure is directed to an electrosurgical blade configured to couple to an RF electrosurgical instrument. The electrosurgical blade includes a proximal portion configured to couple to a blade receptacle of an RF electrosurgical instrument, a coagulation section extending distally from the proximal portion, a blade edge defined around a periphery of the electrosurgical blade, and a ramped surface extending between the coagulation section and the blade edge. The blade edge includes a right-angled tip and is defined by a first side extending longitudinally, a second side extending longitudinally and having a curved portion, and a distal side extending laterally.

In an aspect, the right-angled tip of the blade edge is defined at a point where the first side and the distal side meet.

In an aspect, the right-angled tip of the blade edge is configured to transmit a higher RF concentration than the coagulation section to easily start a transection.

In an aspect, an insulative guard is disposed around at least a portion of the proximal portion.

In an aspect, a coating is disposed around at least an exterior surface of the coagulation section or an exterior surface of the ramped surface. A thickness of the coating disposed around the exterior surface of the coagulation section may be non-uniform or uniform. Additionally or alternatively, a thickness of the coating disposed around the exterior surface of the ramped surface is non-uniform.

In another aspect of the present disclosure, an RF electrosurgical instrument is provided. The RF electrosurgical instrument includes a blade receptacle and an electrosurgical blade operatively coupled thereto. The electrosurgical blade includes a proximal portion configured to couple to a blade receptacle of an RF electrosurgical instrument, a coagulation section extending distally from the proximal portion, a blade edge defined around a periphery of the electrosurgical blade, and a ramped surface extending between the coagulation section and the blade edge. The blade edge includes a right-angled tip and is defined by a first side extending longitudinally, a second side extending longitudinally and having a curved portion, and a distal side extending laterally.

In an aspect, the right-angled tip of the blade edge is defined at a point where the first side and the distal side meet.

In an aspect, the right-angled tip of the blade edge is configured to transmit a higher RF concentration than the coagulation section to easily start a transection.

In an aspect, an insulative guard is disposed around at least a portion of the proximal portion.

In an aspect, a coating is disposed around at least an exterior surface of the coagulation section or an exterior surface of the ramped surface. A thickness of the coating disposed around the exterior surface of the coagulation section may be non-uniform or uniform. Additionally or alternatively, a thickness of the coating disposed around the exterior surface of the ramped surface is non-uniform.

In yet another aspect of the present disclosure, an electrosurgical system is provided. The electrosurgical system includes an electrosurgical generator configured to generate RF electrosurgical energy and an RF electrosurgical instrument configured to couple to the electrosurgical generator and transmit RF electrosurgical energy to tissue. The RF electrosurgical instrument includes a blade receptacle and an electrosurgical blade operatively coupled thereto. The electrosurgical blade includes a proximal portion configured to couple to a blade receptacle of an RF electrosurgical instrument, a coagulation section extending distally from the proximal portion, a blade edge defined around a periphery of the electrosurgical blade, and a ramped surface extending between the coagulation section and the blade edge. The blade edge includes a right-angled tip and is defined by a first side extending longitudinally, a second side extending longitudinally and having a curved portion, and a distal side extending laterally.

In an aspect, the right-angled tip of the blade edge is defined at a point where the first side and the distal side meet.

In an aspect, the right-angled tip of the blade edge is configured to transmit a higher RF concentration than the coagulation section to easily start a transection.

In an aspect, an insulative guard is disposed around at least a portion of the proximal portion.

In an aspect, a coating is disposed around at least an exterior surface of the coagulation section or an exterior surface of the ramped surface. A thickness of the coating disposed around the exterior surface of the coagulation section may be non-uniform or uniform. Additionally or alternatively, a thickness of the coating disposed around the exterior surface of the ramped surface is non-uniform.

BRIEF DESCRIPTION OF THE DRAWINGS

Various embodiments of the present disclosure are described hereinbelow with references to the drawings, wherein.

DETAILED DESCRIPTION

Figure 1:
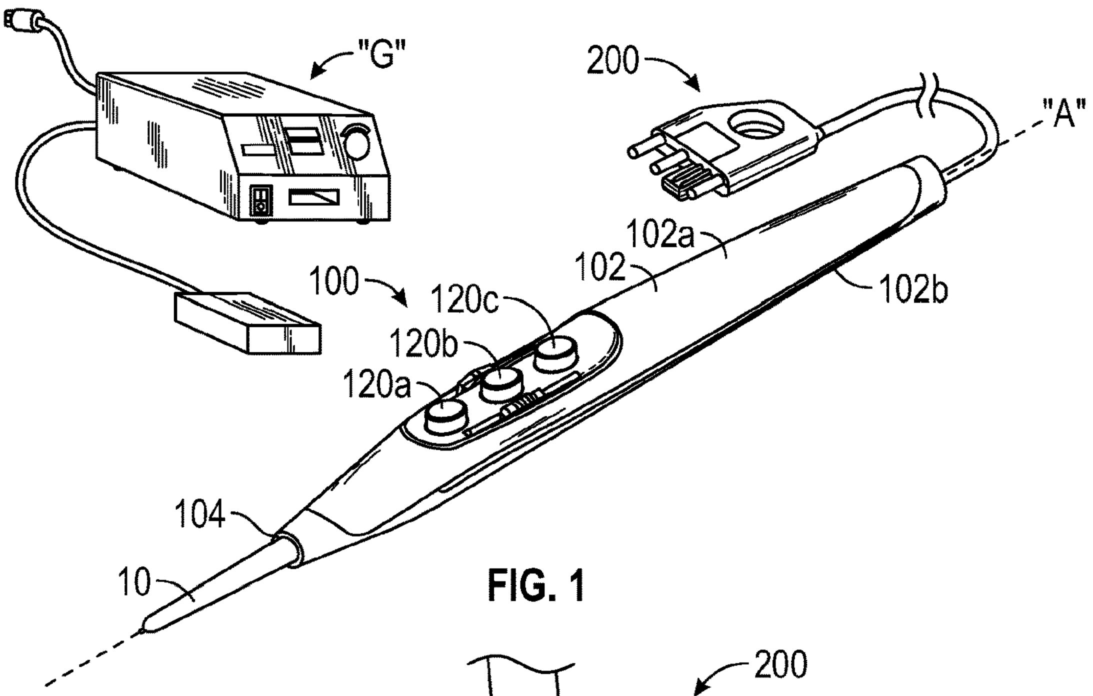
FIG. 1. is a perspective view of an electrosurgical system including a generator and an electrosurgical pencil having an electrosurgical blade electrode in accordance with an embodiment of the present disclosure.

Particular embodiments of the presently disclosed electrosurgical blade electrodes are described in detail with reference to the figures wherein like reference numerals identify similar or identical elements. As used herein, the term "distal" refers to that portion which is further from the user while the term "proximal" refers to that portion which is closer to the user or surgeon.

The following aspects of electrosurgical instruments, and in particular, electrosurgical blade electrodes for electrosurgical instruments, incorporate features to enable fine precision dissection while still maintaining the coagulation capabilities of the blade electrodes. In particular, aspects of electrosurgical blade electrodes disclosed herein include structural features and properties that enable precision dissection of tissue, improving maneuverability of the electrode though tissue and improving safety, for example, by providing tactile features to the user or robotic system at set depths through tissue, by incorporating coatings, and/or by having specific configurations and dimensions that demand lower radiofrequency power settings. Some aspects of electrosurgical blade electrode designs disclosed herein offer a significantly reduced section for precision on the edge of the blade, then two semi-circular cut outs that also provide the tactile feedback for detecting the depth the blade electrode during tissue dissection. The reduced width of the cross section at this location improves the maneuverability of the blade and ultimately the instrument.

Although the following disclosure describes the electrosurgical blade electrodes as being used with a handheld pencil-type electrosurgical instrument, it is understood that the benefits of the structural features of all of the aspects of the electrosurgical blade electrodes disclosed herein may be realized by robotic surgical systems, and the following disclosure is not intended to be limiting.

FIG. 1 sets forth a side, perspective view of an electrosurgical system including an RF electrosurgical generator "G" and RF electrosurgical instrument 100 configured to couple to the RF electrosurgical generator "G" via a plug assembly 200. The RF electrosurgical generator "G" generates RF electrosurgical energy which is configured to be transmitted to tissue via RF electrosurgical instrument 100. To this end, RF electrosurgical instrument 100 includes an electrosurgical blade electrode 10 constructed in accordance with the aspects of the present disclosure.

As illustrated in FIG. 1, RF electrosurgical instrument 100 includes an elongated housing 102 having a top-half shell portion 102*a* and a bottom-half shell portion 102*b*. RF electrosurgical instrument 100 includes a blade receptacle 104 disposed at a distal end of housing 102 configured to operatively and removably connect to a replaceable electrosurgical blade electrode 10. RF electrosurgical instrument 100 includes one or more activation switches (three activation switches 120*a*-120*c* are shown). Each activation switch 120*a*-120*c* controls the transmission of RF electrical energy supplied from RF electrosurgical generator "G" to electrosurgical blade electrode 10 at different power levels or signals. For example, activation of activation switch 120*c* may be configured to provide a high voltage coagulation signal.

For a more detailed description of the RF electrosurgical instrument 100 including operative components associated therewith, reference is made to commonly-owned U.S. Pat. No. 7,879,033, entitled "Electrosurgical Pencil with Advanced ES Controls," the entire contents of which are incorporated by reference herein.

Figure 2A:
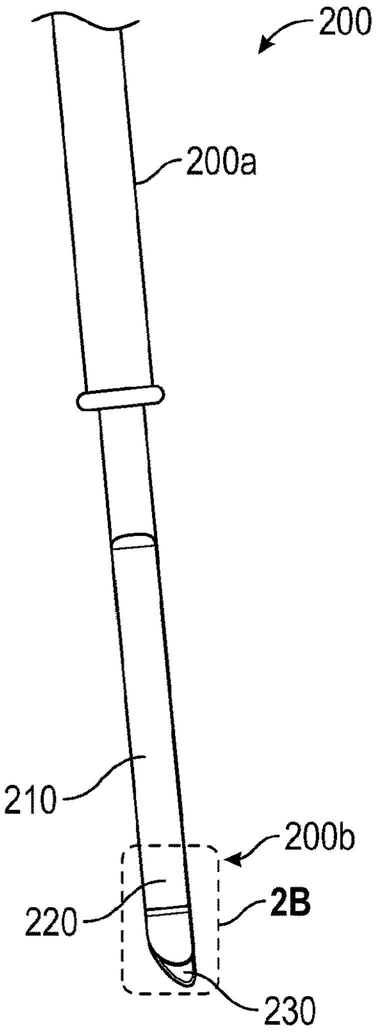
FIG. 2A is top perspective view of an electrosurgical blade electrode for use with an electrosurgical pencil of FIG. 1.
Figure 2B:
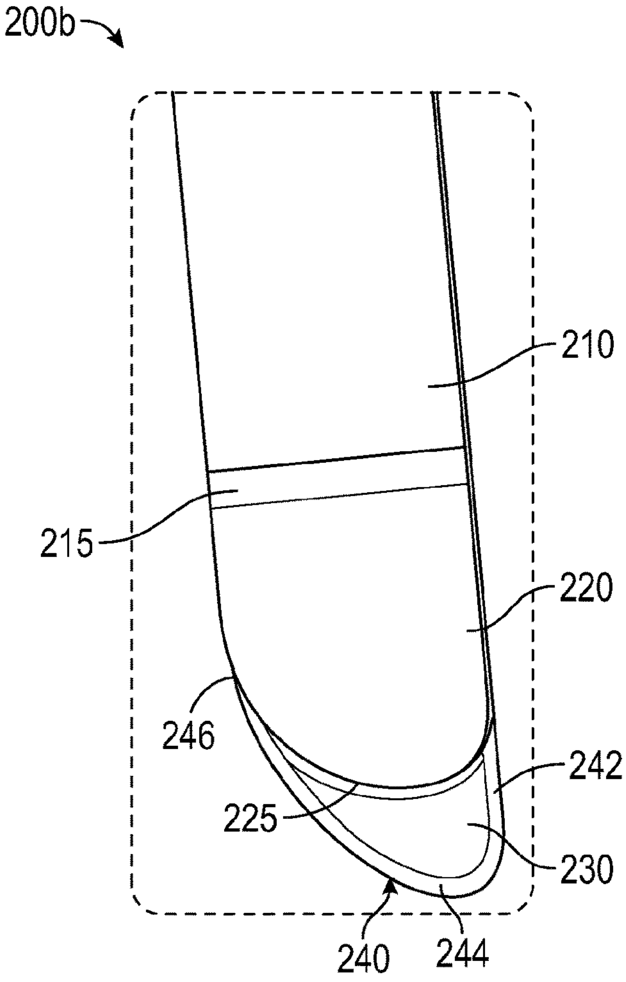
FIG. 2B is an enlarged view of the indicated area of detail of FIG. 2A showing a distal portion of the electrosurgical blade electrode of FIG. 2A.
Figure 2C:
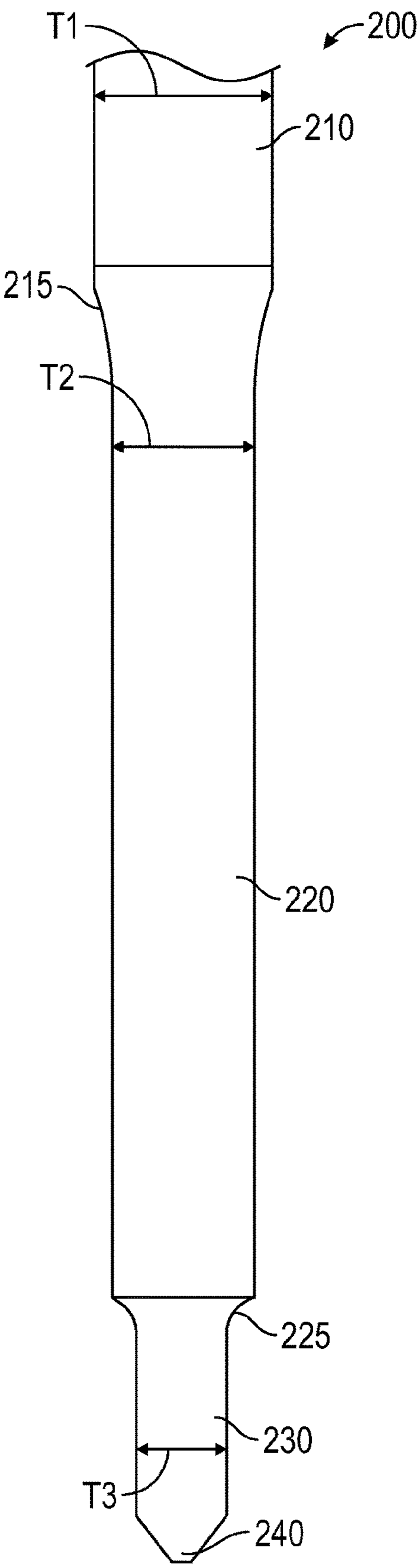
FIG. 2C is a side, cross-sectional view of the electrosurgical blade electrode of FIG. 2A.

With reference now to FIGS. 2A-2C electrosurgical blade electrode 10 will be described in detail as electrosurgical blade 200. Electrosurgical blade 200 may be fabricated from a conductive type material, such as, for example, stainless steel, or may be coated entirely or on selective portions thereof with an electrically conductive material.

Electrosurgical blade 200 may include a layer of insulative coating that may be applied evenly over the entire surface of electrosurgical blade 200. Conversely, insulative coating may be applied in a non-even fashion. More particularly, electrosurgical blade 200 may include portions (e.g., areas that are intended to emanate electrosurgical energy to a tissue site) that have less insulative coating than other areas of the electrosurgical blade 200 (e.g., areas that are not intended to emanate electrosurgical energy to a tissue site or are intended to emanate a lower level of electrosurgical energy to a tissue site). The insulative coating may be made from any suitable material including but not limited to Teflon® coatings, Teflon® polymers, silicone and the like.

As noted above, electrosurgical blade 200 operatively and removably connects to blade receptacle 104 of RF electrosurgical instrument 100 (FIG. 1). To this end, a proximal portion 200*a* of electrosurgical blade 200 is selectively retained by receptacle 104 within the distal end of housing 102. Electrosurgical blade 200 extends distally beyond receptacle 104 and transmits RF electrosurgical energy to tissue during use.

Electrosurgical blade 200 includes a first section 210, a second section 220 extending distally from the first section 210, a third section 230 extending distally from the second section 220, and a blade edge 240 disposed along a peripheral edge of the third section 230. First section 210 of electrosurgical blade 200 has a first thickness T1 and second section 220 of electrosurgical blade 200 has a second thickness T2 which is less than the first thickness T1 of first section 210. The greater thickness T1 of first section 210, relative to the lesser thickness T2 of second section 220, provides the function of limiting the amount of RF electrosurgical energy emitted to tissue from the first section 210 relative to the amount of RF electrosurgical energy emitted to tissue from the second section 220, when the RF electrosurgical energy is transmitted to the electrosurgical blade 200.

Additionally, the difference between the thickness T1 of first section 210 and thickness T2 of second section 220 defines a first step 215 between first section 210 and second section 220 of electrosurgical blade 200. First step 215 may be a ramped surface defined between the surface of first section 210 and the surface of second section 220. Alternatively, first step 215 may be a non-ramped surface, that is, a surface disposed perpendicular to the parallel planes of the surface of the first section 210 and the surface of the second section 220. Additionally, first step 215 may define an axis that is entirely perpendicular to a longitudinal axis defined by electrosurgical blade 200 (shown in FIG. 2B), or alternatively, may define an axis that is not substantially perpendicular to the longitudinal axis of electrosurgical blade 200 (not shown).

First step 215 provides the user with tactile feedback as electrosurgical blade 200 is penetrating deeper through tissue. In particular, after electrosurgical blade 200 is initially penetrated through tissue, the further penetration through the tissue (e.g., after the first few millimeters of tissue) is alerted to the user via the tactile feedback caused by the tissue abutting against first step 215. In hand-held surgical applications, the user will feel the tactile feedback enabled by first step 215 as the user penetrates further through the tissue and tissue abuts first step 215. In robotic surgical applications, the tactile feedback caused by tissue pressing against first step 215 generates a peak in resistance measured by sensors which can be used to determine that tissue is abutting first step 215 or that first step 215 has passed through tissue.

Third section 230 of electrosurgical blade 200 has a third thickness T3 which is less than the second thickness T2 of second section 220. The greater thickness T2 of second section 220, relative to the lesser thickness T3 of third section 230, provides the function of limiting the amount of RF electrosurgical energy emitted to tissue from the second section 220 relative to the amount of RF electrosurgical energy emitted to tissue from the third section 230, when the RF electrosurgical energy is transmitted to the electrosurgical blade 200.

Additionally, the difference between the thickness T3 of third section 230 and thickness T2 of second section 220 defines a second step 225 between third section 230 and second section 220 of electrosurgical blade 200. Second step 225 may be a ramped surface defined between the surface of third section 230 and the surface of second section 220. Alternatively, second step 225 may be a non-ramped surface, that is, a surface disposed perpendicular to the parallel planes of the surface of the third section 230 and the surface of the second section 220. Additionally, second step 225 may define an axis that is entirely perpendicular to a longitudinal axis defined by electrosurgical blade 200 (not shown), may define an axis that is partially perpendicular to the longitudinal axis of electrosurgical blade 200 (not shown), or alternatively, may define a particular shape, for example, the "U" shape shown in FIG. 2B.

Second step 225 provides the user with tactile feedback as electrosurgical blade 200 is penetrating deeper through tissue. In particular, after blade edge 240 of electrosurgical blade 200 is initially penetrated through tissue to create an incision, the further penetration through the tissue (e.g., immediately following the penetration of tissue) is alerted to the user via the tactile feedback caused by the tissue abutting second step 225. In hand-held surgical applications, the user will feel the tactile feedback enabled by second step 225 immediately following the initial incision through tissue and tissue abuts second step 225. In robotic surgical applications, the tactile feedback caused by tissue against second step 225 generates a peak in resistance measured by sensors which can be used to determine that tissue is abutting second step 225 or that second step 225 has passed through tissue.

Third section 230 of electrosurgical blade 200 includes a blade edge 240 disposed at a distal portion thereof. Blade edge 240 is defined by a first side 242, second side 244, and third side 246. In an aspect, the length of first side 242 is greater than the length of third side 246. Additionally, or alternatively, any or all of first side 242, second side 244, or third side 246 may be a blunt edge or a sharpened edge.

Although the structural features of first section 210, second section 220, and third section 230 of electrosurgical blade 200 are illustrated and described from the perspective of the topside of electrosurgical blade 200, it is understood that some or all of the features may also be present on the bottomside of electrosurgical blade 200. Thus, the bottomside of electrosurgical blade 200 may be a planar surface along its length or may include some or all of the features present on the topside thereof.

Figure 3:
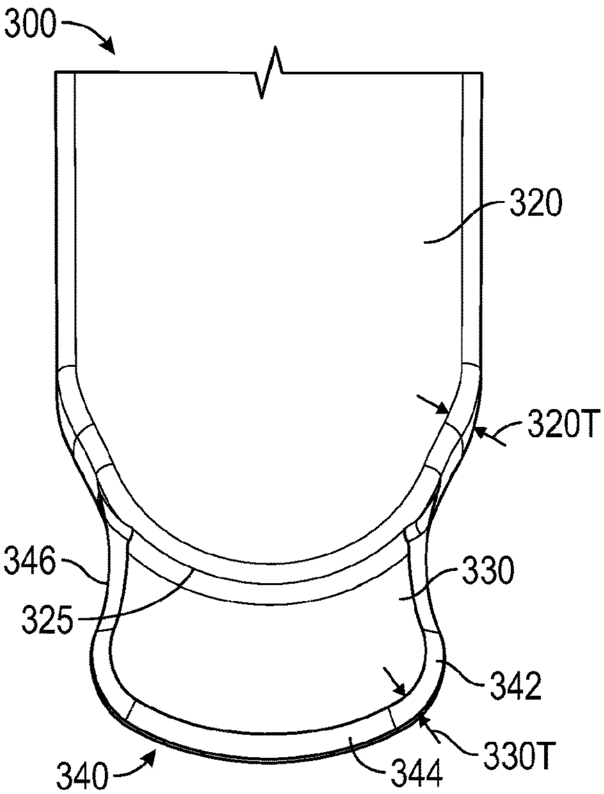
FIG. 3 is a top view of a distal portion of an electrosurgical blade electrode for use with an electrosurgical pencil of FIG. 1 in accordance with another aspect of the present disclosure.

Turning now to FIG. 3, another electrosurgical blade electrode 10 will be described in detail as electrosurgical blade 300. Electrosurgical blade 300 may be fabricated from a conductive type material, such as, for example, stainless steel, or may be coated entirely or on selective portions thereof with an electrically conductive material.

Electrosurgical blade 300 may include a layer of insulative coating that may be applied evenly over the entire surface of electrosurgical blade 300. Conversely, the insulative coating may be applied in a non-even fashion. More particularly, electrosurgical blade 300 may include portions (e.g., areas that are intended to emanate electrosurgical energy to a tissue site) that have less insulative coating than other areas of the electrosurgical blade 300 (e.g., areas that are not intended to emanate electrosurgical energy to a tissue site or are intended to emanate a lower level of electrosurgical energy to a tissue site). The insulative coating may be made from any suitable material including but not limited to Teflon® coatings, Teflon® polymers, silicone and the like.

As noted above, electrosurgical blade 300 operatively and removably connects to blade receptacle 104 of RF electrosurgical instrument 100 (FIG. 1). To this end, a proximal portion (not shown) of electrosurgical blade 300 is selectively retained by receptacle 104 within the distal end of housing 102. Electrosurgical blade 300 extends distally beyond receptacle 104 and transmits RF electrosurgical energy to tissue during use.

Electrosurgical blade 300 includes a first section (not shown), a second section 320 extending distally from the first section, a third section 330 extending distally from the second section 320, and a blade edge 340 disposed along a peripheral edge of the third section 330. Although not explicitly shown, like electrosurgical blade 200, first section of electrosurgical blade 300 has a first thickness (not shown) and second section 320 of electrosurgical blade 300 has a second thickness 320T which is less than the first thickness of first section. The greater thickness of the first section, relative to the lesser thickness 320T of second section 320, provides the function of limiting the amount of RF electrosurgical energy emitted to tissue from the first section relative to the amount of RF electrosurgical energy emitted to tissue from the second section 320, when the RF electrosurgical energy is transmitted to the electrosurgical blade 300.

Additionally, the difference between the thickness of the first section and thickness 320T of second section 320 defines a first step (not shown) between the first section and second section 320 of electrosurgical blade 300. First step (not shown) may be a ramped surface defined between the surface of the first section and the surface of second section 320. Alternatively, first step may be a non-ramped surface, that is, a surface disposed perpendicular to the parallel planes of the surface of the first section and the surface of the second section 320.

First step provides the user with tactile feedback as electrosurgical blade 300 is penetrating deeper through tissue. In particular, after electrosurgical blade 300 is initially penetrated through tissue, the further penetration through the tissue (e.g., after the first few millimeters of tissue) is alerted to the user via the tactile feedback caused by the tissue abutting against first step. In hand-held surgical applications, the user will feel the tactile feedback enabled by first step as the user penetrates further through the tissue and tissue abuts first step. In robotic surgical applications, the tactile feedback caused by tissue against first step generates a peak in resistance measured by sensors which can be used to determine that tissue is abutting first step or that first step has passed through tissue.

Third section 330 of electrosurgical blade 300 has a third thickness 330T which is less than the second thickness 320T of second section 320. The greater thickness 320T of second section 320, relative to the lesser thickness 330T of third section 330, provides the function of limiting the amount of RF electrosurgical energy emitted to tissue from the second section 320 relative to the amount of RF electrosurgical energy emitted to tissue from the third section 330, when the RF electrosurgical energy is transmitted to the electrosurgical blade 300.

Additionally, the difference between the thickness 330T of third section 330 and thickness 320T of second section 320 defines a second step 325 between third section 330 and second section 320 of electrosurgical blade 300. Second step 325 may be a ramped surface defined between the surface of third section 330 and the surface of second section 320. Alternatively, second step 325 may be a non-ramped surface, that is, a surface disposed perpendicular to the parallel planes of the surface of the third section 330 and the surface of the second section 320. Additionally, second step 325 may define an axis that is entirely perpendicular to a longitudinal axis defined by electrosurgical blade 300 (not shown), may define an axis that is partially perpendicular to the longitudinal axis of electrosurgical blade 300 (not shown), or alternatively, may define a particular shape, for example, the "U" shape shown in FIG. 3.

Second step 325 provides the user with tactile feedback as electrosurgical blade 300 is penetrating deeper through tissue. In particular, after blade edge 340 of electrosurgical blade 300 is initially penetrated through tissue to create an incision, the further penetration through the tissue (e.g., immediately following the penetration of tissue) is alerted to the user via the tactile feedback caused by the tissue abutting second step 325. In hand-held surgical applications, the user will feel the tactile feedback enabled by second step 325 immediately following the initial incision through tissue and tissue abuts second step 325. In robotic surgical applications, the tactile feedback caused by tissue against second step 325 generates a peak in resistance measured by sensors which can be used to determine that tissue is abutting second step 325 or that second step 325 has passed through tissue.

Third section 330 of electrosurgical blade 300 includes a blade edge 340 disposed at a distal portion thereof. Blade edge 340 is defined by a first side 342, second side 344, and third side 346. In an aspect, the length of first side 342 is equal the length of third side 346. Additionally, either or both of first side 342 or third side 346 may be curved or otherwise arcuate from its proximal end to its distal end as illustrated in FIG. 3. Additionally, or alternatively, any or all of first side 342, second side 344, or third side 346 may be a blunt edge or a sharpened edge.

Although the structural features of second section 320 and third section 330 of electrosurgical blade 300 are illustrated and described from the perspective of the topside of electrosurgical blade 300, it is understood that some or all of the features may also be present on the bottomside of electrosurgical blade 300. Thus, the bottomside of electrosurgical blade 300 may be a planar surface along its length or may include some or all of the features present on the topside thereof.

Figure 4:
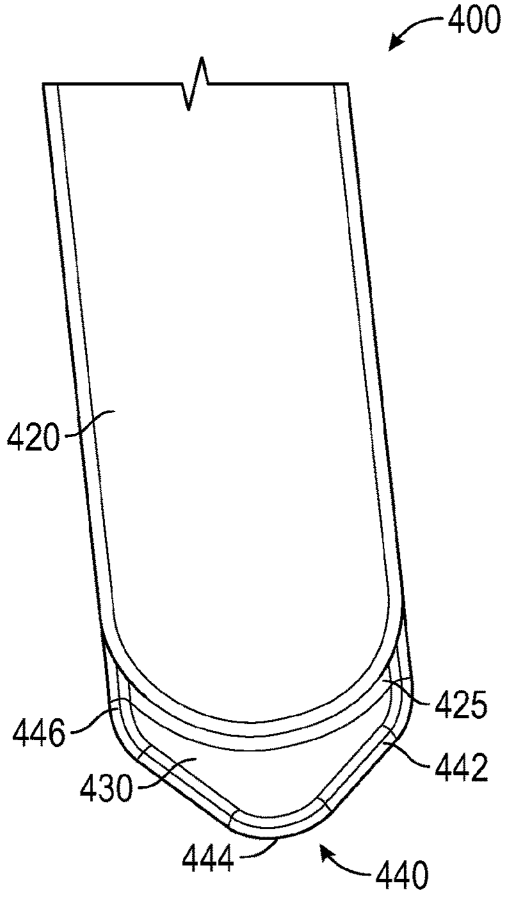
FIG. 4 is a top, perspective, view of a distal portion of an electrosurgical blade electrode for use with an electrosurgical pencil of FIG. 1 in accordance with another aspect of the present disclosure.

Turning now to FIG. 4, another electrosurgical blade electrode 10 will be described in detail as electrosurgical blade 400. Electrosurgical blade 400 is similar to electrosurgical blade 300 and thus only the differences between the two, generally, will be described. Electrosurgical blade 400 includes a second section 420 which steps down to third section 430 via second step 425. Like second step 325 of electrosurgical blade 300, second step 425 of electrosurgical blade 400 may be "U" shaped as shown in FIG. 4.

Third section 430 of electrosurgical blade 400 includes a blade edge 440. Blade edge 440 includes a first side 442, second side 444, and third side 446. Respective proximal portions of first side 442 and third side 446 are contiguous with the sides of second section 420. Mid portions of first side 442 and third side 446 taper inward toward a longitudinal axis defined by electrosurgical blade 400 to meet at second side 444. Second side 444 may be rounded as shown in FIG. 4, or alternatively, may be a single point in which first side 442 and third side 446 meet thereby defining a pointed tip.

Although the structural features of second section 420 and third section 430 of electrosurgical blade 400 are illustrated and described from the perspective of the topside of electrosurgical blade 400, it is understood that some or all of the features may also be present on the bottomside of electrosurgical blade 400. Thus, the bottomside of electrosurgical blade 400 may be a planar surface along its length or may include some or all of the features present on the topside thereof.

Figure 5:
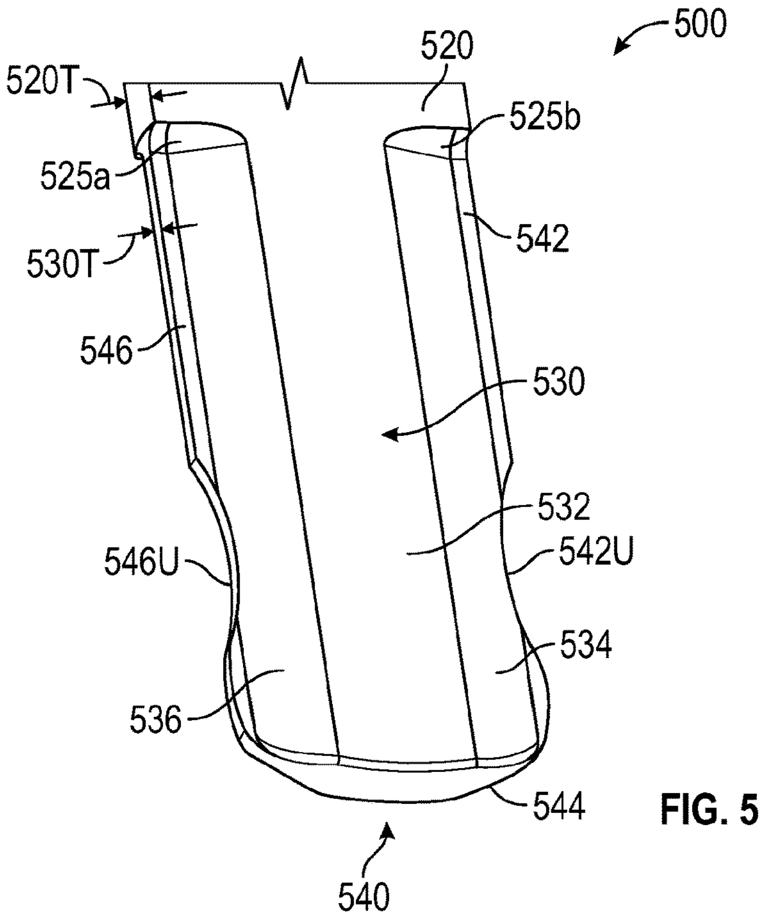
FIG. 5 is a top, perspective, view of a distal portion of an electrosurgical blade electrode for use with an electrosurgical pencil of FIG. 1 in accordance with another aspect of the present disclosure.

Turning now to FIG. 5, another electrosurgical blade electrode 10 will be described in detail as electrosurgical blade 500. Electrosurgical blade 500 may be fabricated from a conductive type material, such as, for example, stainless steel, or may be coated entirely or on selective portions thereof with an electrically conductive material.

As described in greater detail below, electrosurgical blade 500 offers a significantly reduced section for precision on the edge of the blade, then two semi-circular cut outs that also provides the tactile feedback for detecting the depth of the electrosurgical blade 500 during tissue dissection. The reduced width of the cross section at this location improves the maneuverability when positioned through tissue and for moving along tissue.

Electrosurgical blade 500 may include a layer of insulative coating that may be applied evenly over the entire surface of electrosurgical blade 500. Conversely, insulative coating may be applied in a non-even fashion. More particularly, electrosurgical blade 500 may include portions (e.g., areas that are intended to emanate electrosurgical energy to a tissue site) that have less insulative coating than other areas of the electrosurgical blade 500 (e.g., areas that are not intended to emanate electrosurgical energy to a tissue site or are intended to emanate a lower level of electrosurgical energy to a tissue site). The insulative coating may be made from any suitable material including but not limited to Teflon® coatings, Teflon® polymers, silicone and the like.

As noted above, electrosurgical blade 500 operatively and removably connects to blade receptacle 104 of RF electrosurgical instrument 100 (FIG. 1). To this end, a proximal portion (not shown) of electrosurgical blade 500 is selectively retained by receptacle 104 within the distal end of housing 102. Electrosurgical blade 500 extends distally beyond receptacle 104 and transmits RF electrosurgical energy to tissue during use.

Electrosurgical blade 500 includes a first section (not shown), a second section 520 extending distally from the first section, a third section 530 extending distally from the second section 520, and a blade edge 540 disposed along a peripheral edge of the third section 530. Although not explicitly shown, like electrosurgical blade 200, first section of electrosurgical blade 500 has a first thickness (not shown) and second section 520 of electrosurgical blade 500 has a second thickness 520T which is less than the first thickness of first section. The greater thickness of the first section, relative to the lesser thickness 520T of second section 520, provides the function of limiting the amount of RF electrosurgical energy emitted to tissue from the first section relative to the amount of RF electrosurgical energy emitted to tissue from the second section 520, when the RF electrosurgical energy is transmitted to the electrosurgical blade 500.

Additionally, the difference between the thickness of the first section and thickness 520T of second section 520 defines a first step (not shown) between the first section and second section 520 of electrosurgical blade 500. First step (not shown) may be a ramped surface defined between the surface of the first section and the surface of second section 520. Alternatively, first step may be a non-ramped surface, that is, a surface disposed perpendicular to the parallel planes of the surface of the first section and the surface of the second section 520.

First step provides the user with tactile feedback as electrosurgical blade 500 is penetrating deeper through tissue. In particular, after electrosurgical blade 500 is initially penetrated through tissue, the further penetration through the tissue (e.g., after the first few millimeters of tissue) is alerted to the user via the tactile feedback caused by the tissue abutting against first step. In hand-held surgical applications, the user will feel the tactile feedback enabled by first step as the user penetrates further through the tissue and tissue abuts first step. In robotic surgical applications, the tactile feedback caused by tissue against first step generates a peak in resistance measured by sensors which can be used to determine that tissue is abutting first step or that first step has passed through tissue.

Third section 530 of electrosurgical blade 500 is composed of a midsection 532 and a first side section 534 on one side of midsection 532 and a second side section 536 on the other side of midsection 532. Midsection 532 extends the length of third section 530. In an aspect, the surface of midsection 532 is coplanar with the surface of second section 520. First side section 534 extends outward from one side of midsection 532 forming a ramped surface therefrom and defining a left second step 525*a* between it and second section 520. Similarly, second side section 536 extends outward from the other side of midsection 532 forming another ramped surface therefrom and defining a right second step 525*b* between it and second section 520.

Third section 530 also includes a blade edge 540 defined about its periphery. Blade edge 540 is defined by first side 542, second side 544, and third side 546. As shown in FIG. 5, second side 544 may be blunt and first side 542 and third side 546 may be equal in length. Additionally, at least one of first side 542 or third side 546 of blade edge 540 (and/or first side section 534 or second side section 536) may have semi-circular cutouts 542*u*, 546*u* disposed along a length thereof. Semi-circular cutouts 542*u*, 546*u* create a region along third section 530 with a narrower width relative to the remaining portions of third section 530. This narrower width provides the tactile feedback for detecting the depth the electrosurgical blade 500 during tissue dissection and improves its maneuverability.

Although the structural features of second section 520 and third section 530 of electrosurgical blade 500 are illustrated and described from the perspective of the topside of electrosurgical blade 500, it is understood that some or all of the features may also be present on the bottomside of electrosurgical blade 500. Thus, the bottomside of electrosurgical blade 500 may be a planar surface along its length or may include some or all of the features present on the topside thereof.

Each of first side section 534 and second side section 536 of third section 530 has a third thickness 530T which is less than the second thickness 520T of second section 520. Midsection 532 of third section 530 has a substantially similar thickness to that of second section 520. The greater thickness 520T of second section 520, relative to the lesser thickness 530T of the sides of third section 530, provides the function of limiting the amount of RF electrosurgical energy emitted to tissue from the second section 520 relative to the amount of RF electrosurgical energy emitted to tissue from the sides of third section 530, when the RF electrosurgical energy is transmitted to the electrosurgical blade 500.

Additionally, the difference between the thickness 530T of the sides of third section 530 and thickness 520T of second section 520 defines respective steps 525*a*, 525*b* between third section 530 and second section 520 of electrosurgical blade 500. One or both of steps 525*a*, 525*b* may be a ramped surface defined between the side surface of third section 530 and the surface of second section 320. Alternatively, second step 525 may be a non-ramped surface, that is, a surface disposed perpendicular to the parallel planes of the side surface of the third section 530 and the surface of the second section 520. Additionally, one or both of steps 525*a*, 525*b* may define an axis that is entirely perpendicular to a longitudinal axis defined by electrosurgical blade 500 (shown in FIG. 5), may define an axis that is partially perpendicular to the longitudinal axis of electrosurgical blade 500 (not shown), or alternatively, may define a particular shape.

Steps 525*a*, 525*b* provide the user with tactile feedback as electrosurgical blade 500 is penetrating deeper through tissue. In particular, after blade edge 540 of electrosurgical blade 500 is initially penetrated through tissue to create an incision, the further penetration through the tissue (e.g., immediately following the penetration of tissue) is alerted to the user via the tactile feedback caused by the tissue abutting either one of steps 525*a*, 525*b*. In hand-held surgical applications, the user will feel the tactile feedback enabled by either one of steps 525*a*, 525*b* immediately following the initial incision through tissue and tissue abuts either one of steps 525*a*, 525*b*. In robotic surgical applications, the tactile feedback caused by tissue against either one of steps 525*a*, 525*b* generates a peak in resistance measured by sensors which can be used to determine that tissue is abutting either one of steps 525*a*, 525*b* or that either one of steps 525*a*, 525*b* has passed through tissue.

Figure 6:
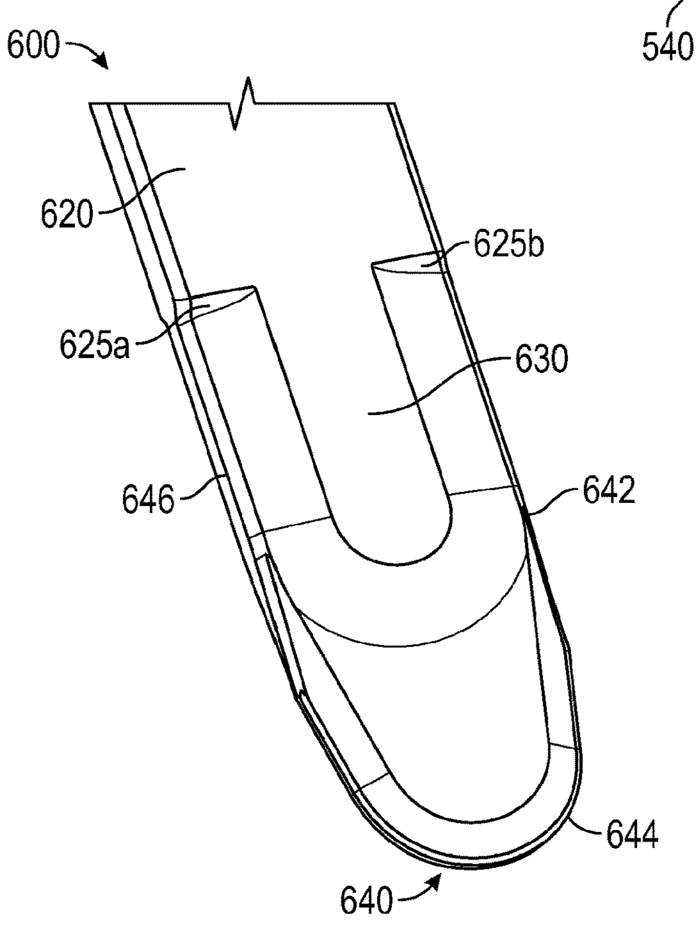
FIG. 6 is a top, perspective, view of a distal portion of an electrosurgical blade electrode for use with an electrosurgical pencil of FIG. 1 in accordance with another aspect of the present disclosure.

Turning now to FIG. 6, another electrosurgical blade electrode 10 will be described in detail as electrosurgical blade 600. Electrosurgical blade 600 may be fabricated from a conductive type material, such as, for example, stainless steel, or may be coated entirely or on selective portions thereof with an electrically conductive material. Electrosurgical blade 600 is similar to the other electrosurgical blades described herein and therefore only the differences therefrom will be described.

Electrosurgical blade 600 includes a second section 620 and a third section 630 extending distally from the second section 620. A blade edge 640 is defined about the periphery of third section 630. Additionally, third section 630 includes a "U" shaped midsection, a distal portion of which ramps down to blade edge 640. Like electrosurgical blade 500, electrosurgical blade 600 includes steps 625*a*, 625*b* on each side thereof. First side 642 of blade edge 640 and third side 646 of blade edge 640 are substantially equal in length and extend distally, tapering inward to meet at second side 644.

Although the structural features of second section 620 and third section 630 of electrosurgical blade 600 are illustrated and described from the perspective of the topside of electrosurgical blade 600, it is understood that some or all of the features may also be present on the bottomside of electrosurgical blade 600. Thus, the bottomside of electrosurgical blade 600 may be a planar surface along its length or may include some or all of the features present on the topside thereof.

Figure 7A:
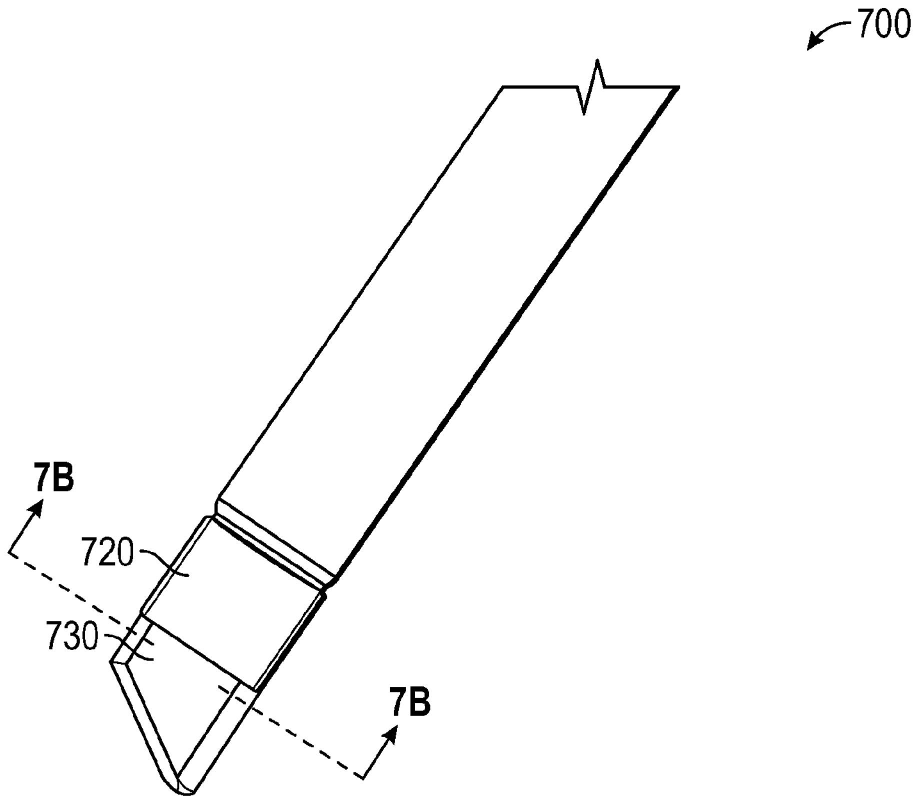
FIG. 7A is a top, perspective, view of a distal portion of an electrosurgical blade electrode for use with an electrosurgical pencil of FIG. 1 in accordance with another aspect of the present disclosure.
Figure 7B:
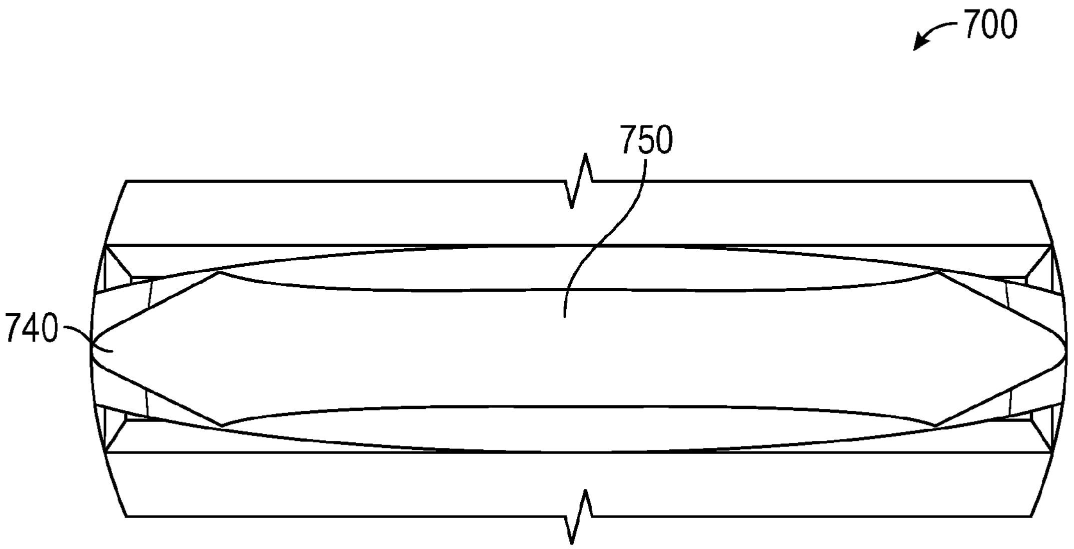
FIG. 7B is a front, cross-sectional view of the electrosurgical blade electrode of FIG. 7A.

Turning now to FIGS. 7A-7B, another electrosurgical blade electrode 10 will be described in detail as electrosurgical blade 700. Electrosurgical blade 700 may be fabricated from a conductive type material, such as, for example, stainless steel, or may be coated entirely or on selective portions thereof with an electrically conductive material. Electrosurgical blade 700 is similar to the other electrosurgical blades described herein and therefore only the differences therefrom will be described.

Electrosurgical blade 700 includes a second section 720 and a third section 730 extending distally from the second section 720. In an aspect, the second section 720 is designed for coagulating tissue and the third section 730 is designed for cutting tissue. Thus, in one aspect, the area of the surface intended to contact tissue of the second section 720 is maximized, while the area of the surface intended to contact tissue in the third section 730 is minimized. A blade edge 740 is defined about the periphery of third section 730. Additionally, at least a portion of third section 630 defines a concave profile shown as a shallow elliptical pocket 750. The design of the shallow elliptical pocket 750 improves performance of electrosurgical blade 700 by reducing surface contact of electrosurgical blade 700 with tissue in portions that are not desired to contact tissue. Electrosurgical blade 700 optimizes the surface in contact with tissue immediately adjacent to blade edge 740. As the tissue is divided by blade edge 740, the other surfaces of electrosurgical blade 700 (e.g., shallow elliptical pocket 750) are designed to not electrically or physically be in contact with the tissue, thereby minimizing the amount of RF energy that can transfer causing thermal spread and tissue sticking.

As shown in FIG. 7B, an elliptical pocket 750 is defined so that the blade edge 740 divides the tissue and the concave void defined by elliptical pockets 750 prevent tissue from contacting the surface (e.g., surface of third section 730) of electrosurgical blade 700. This configuration further minimizes the amount of thermal damage to the tissue, but still allows for hemostasis when the electrosurgical blade 700 is used on its coagulation surfaces (e.g., surfaces defined by second section 720) and to some extent along the elliptical pocket 750 in coagulation mode. This feature also enables improved coating performance by not dragging (or minimizing the contact area of) the hot surfaces of the electrosurgical blade 700 through the tissue.

Although the structural features of second section 720 and third section 730 of electrosurgical blade 700 are illustrated and described from the perspective of the topside of electrosurgical blade 700, it is understood that some or all of the features may also be present on the bottomside of electrosurgical blade 700. Thus, the bottomside of electrosurgical blade 700 may be a planar surface along its length or may include some or all of the features present on the topside thereof.

Figure 8A:
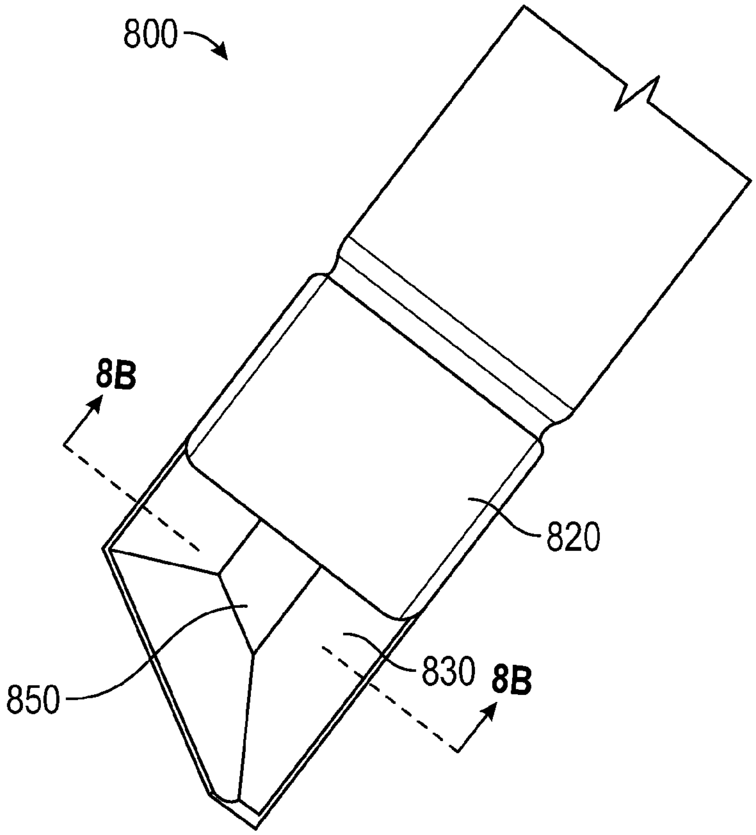
FIG. 8A is a top, perspective, view of a distal portion of an electrosurgical blade electrode for use with an electrosurgical pencil of FIG. 1 in accordance with another aspect of the present disclosure.
Figure 8B:
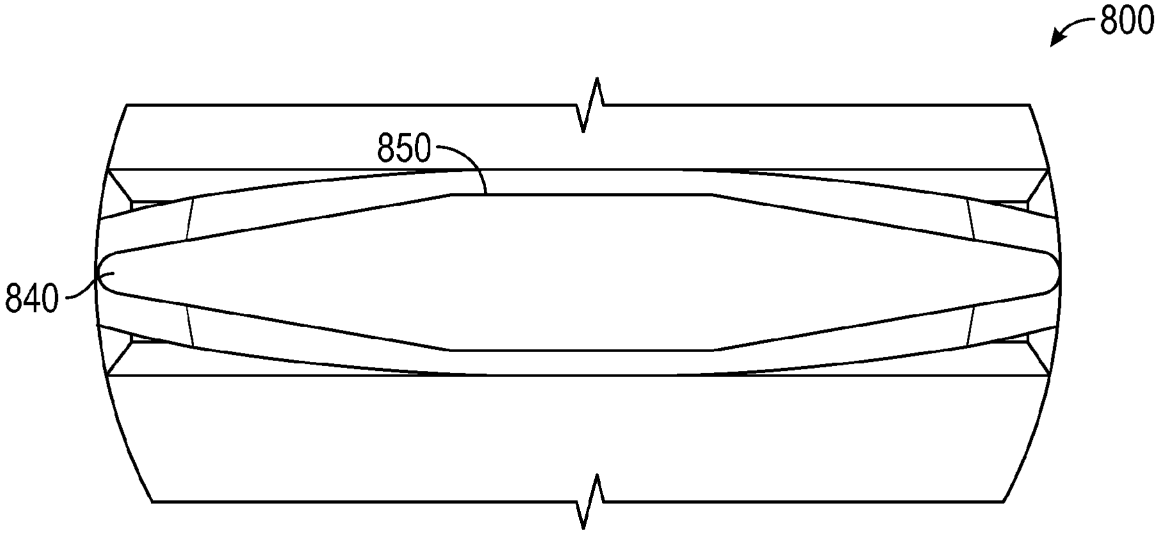
FIG. 8B is a front, cross-sectional view of the electrosurgical blade electrode of FIG. 8A.

Turning now to FIGS. 8A-8B, another electrosurgical blade electrode 10 will be described in detail as electrosurgical blade 800. Electrosurgical blade 800 may be fabricated from a conductive type material, such as, for example, stainless steel, or may be coated entirely or on selective portions thereof with an electrically conductive material. Electrosurgical blade 800 is similar to the other electrosurgical blades described herein and therefore only the differences therefrom will be described.

Electrosurgical blade 800 includes a second section 820 and a third section 830 extending distally from the second section 820. In an aspect, the second section 820 is designed for coagulating tissue and the third section 830 is designed for cutting tissue. Thus, in one aspect, the area of the surface intended to contact tissue of the second section 820 is maximized, while the area of the surface intended to contact tissue in the third section 830 is minimized. A blade edge 840 is defined about the periphery of third section 830. Additionally, at least a portion of third section 830 defines a surface 850 that is minimized in width. The design of the surface 850 having a minimized width improves performance of electrosurgical blade 800 by reducing surface contact of electrosurgical blade 800 with tissue in portions that are not desired to contact tissue. Electrosurgical blade 800 optimizes the surface in contact with tissue immediately adjacent to blade edge 840. As the tissue is divided by blade edge 840, the other surfaces of electrosurgical blade 800 (e.g., surface 850) are designed to minimize the area in which these surfaces contact tissue, thereby minimizing the amount of RF energy that can transfer causing thermal spread and tissue sticking. This feature also enables improved coating performance by not dragging (or minimizing the contact area of) the hot surfaces of the electrosurgical blade 800 through the tissue.

Although the structural features of second section 820 and third section 830 of electrosurgical blade 800 are illustrated and described from the perspective of the topside of electrosurgical blade 800, it is understood that some or all of the features may also be present on the bottomside of electrosurgical blade 800. Thus, the bottomside of electrosurgical blade 800 may be a planar surface along its length or may include some or all of the features present on the topside thereof.

Turning now to FIGS. 9A-9D, another electrosurgical blade electrode 10 will be described in detail as electrosurgical blade 900. Electrosurgical blade 900 may be fabricated from a conductive material, such as, for example, stainless steel, or may be coated entirely or on selective portions thereof with an electrically conductive material. Electrosurgical blade 900 is similar to the above-described electrosurgical blades and therefore only the differences are described below.

Electrosurgical blade 900 extends from an insulative guard 910, or alternatively, the insulative guard 910 is disposed around a proximal portion 900*a* of the electrosurgical blade 900. The insulative guard 910 prevents the electrosurgical blade 900 from cutting too deep into tissue which may cause unintended damage to the tissue layers or organs below the surface tissue. A distal portion 900*b* of electrosurgical blade 900 includes a broad coagulation section 920, extending distally from the proximal portion 900*a*, and a blade edge 940. The coagulation section 920 is designed for coagulating tissue and the blade edge 940 is defined around a perimeter of the electrosurgical blade 900 (e.g., around a perimeter of ramped surfaces 930 extending outwardly from the coagulation section 920) and is designed for cutting tissue. Thus, in one aspect, the area of the surface intended to contact tissue of the coagulation section 920 is maximized.

Figure 9A:
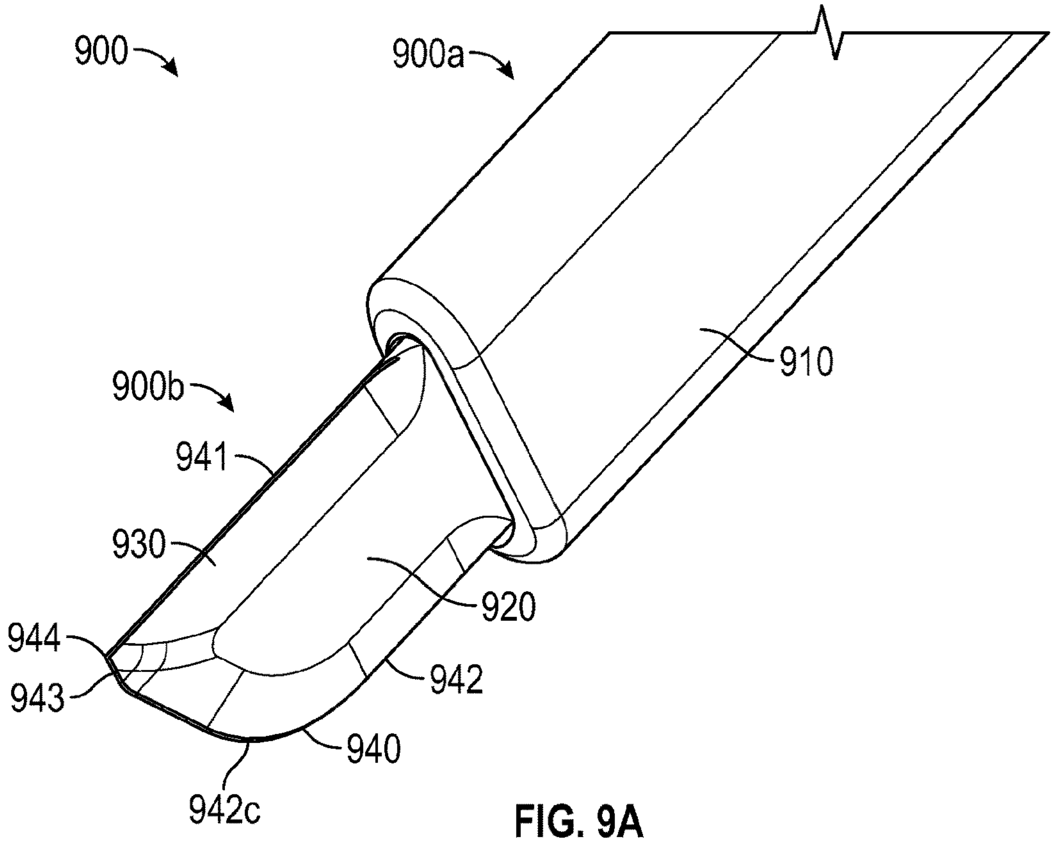
FIG. 9A is a front-side, perspective, view of an electrosurgical blade electrode for use with an electrosurgical pencil of FIG. 1.
Figure 9B:
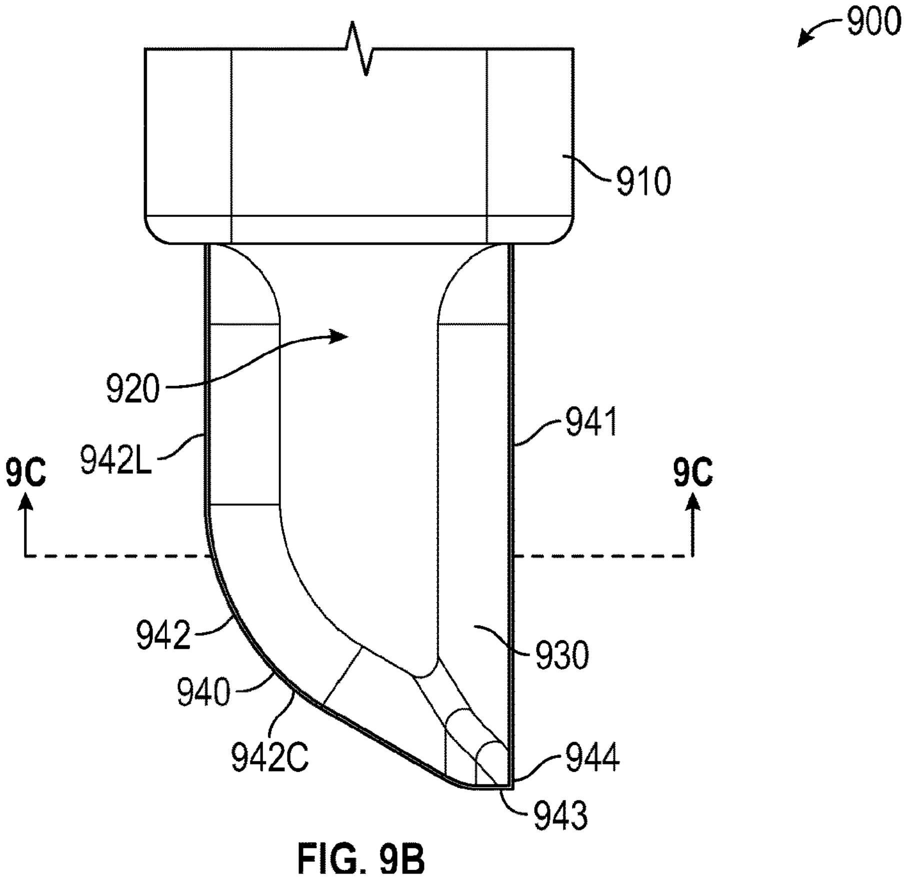
FIG. 9B is a top, perspective, view of a distal portion of the electrosurgical blade electrode of FIG. 9A.

Electrosurgical blade 900 is asymmetric (e.g., not identical on both sides of its centerline). In particular, as shown in FIGS. 9A-9B, blade edge 940 of electrosurgical blade 900 includes a first side 941, a second side 942, and a distal side 943. The first side 941 is linear and extends longitudinally along a length of one side of the electrosurgical blade 900 to the distal side 943, which is also linear and extends laterally and perpendicular to the first side 941, where a right-angled tip 944 is formed at a point in which a distal end of the first side 941 and the distal side 943 meet. The second side 942 includes a linear portion 9421 and a curved portion 942*c* and extends along a length of a second side of the electrosurgical blade 900 where the curved portion 942*c* meets the distal side 943. A ramped surface 930 extends from the coagulation section 920 to the blade edge 940.

The right-angled tip 944 is designed to form a current concentration and enables a surgeon to perform delicate operations on tissue, e.g. precise transection and spot coagulation, while also enabling the surgeon to perform operations at a significantly lower power setting (e.g., 5 W-20 W) due to the current concentration formed at the right-angled tip 944. The curved portion 942*c* of blade edge 940 is designed to leverage the use-habit of traditional cold scalpels which provides the surgeon the ability to perform superficial straight dissection.

Figure 9C:
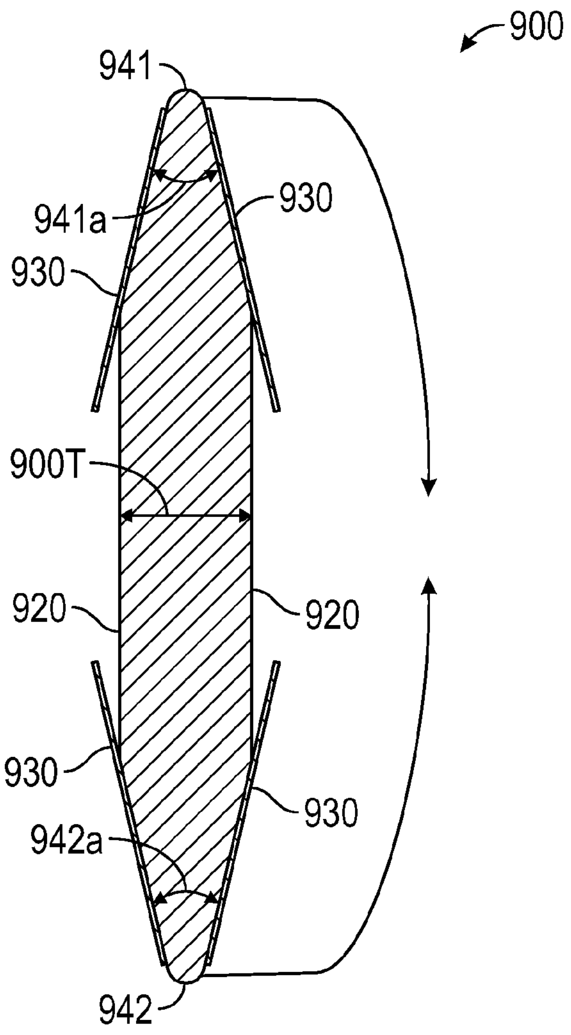
FIG. 9C is a front, cross-sectional view taken across a line 9C-9C of a distal portion of the electrosurgical blade electrode of FIG. 9A.

With reference to FIG. 9C, the electrosurgical blade 900 may have a center thickness 900T ranging between 0.3 mm-0.8 mm, which provides sufficient rigidity to withstand bending forces during operation while also providing sufficient elasticity for a surgeon to intentionally bend the electrosurgical blade 900 when necessary or desired. The upper and lower ramped surfaces 930 extending from the first side 941 define a wedge angle 941*a* and the upper and lower ramped surfaces 930 extending from second side 942 define a wedge angle 942*a*, which may be the same as, or different from, wedge angle 941*a*. In an aspect, either or both of wedge angle 941*a* and wedge angle 942*a* is within the range of 20 degrees to 40 degrees which contributes to the current concentration along first side 941 and second side 942 to enable smooth dissection using first side 941 or second side 942 with a lower power setting.

Figure 9D:
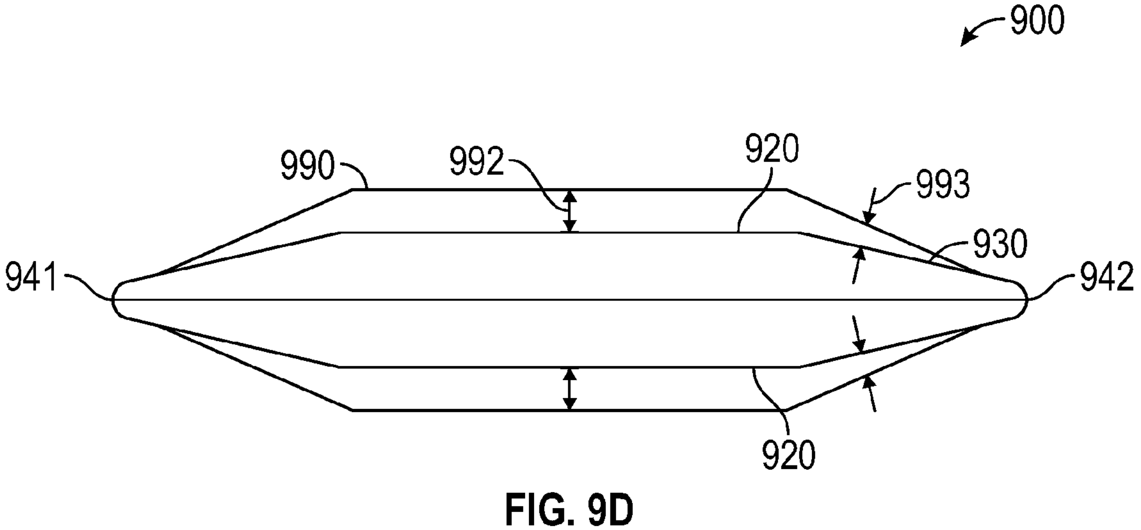
FIG. 9D is a front, cross-sectional view taken across the line 9C-9C of a distal portion of the electrosurgical blade electrode and a coating of the electrosurgical blade electrode of FIG. 9A.

Turning now to FIG. 9D, coating 990 may be disposed around the external surface of electrosurgical blade 900, for example, around at least a portion of the external surface of coagulation section 920, ramped surfaces 930, or blade edge 940. Coating 990 may be an insulative coating, formed of a material having a high impedance in RF and which provides anti-stick performance in high temperatures (e.g., 300 degrees C.). Coating 990 may be formed of at least one of polymers (e.g., PTFE, PFA, etc.) and/or ceramics (e.g., TiN, CrN, Al2O3, etc.). The thickness of coating 900 varies from edge to edge, that is, from first side 941 to second side 942. For example, the thickness of coating 990 may be greater at a center area (e.g., around coagulation section 920) and lower closer to the edges of the electrosurgical blade 900 (e.g., around ramped surface 930 or blade edge 940). In one aspect, the coating 990 has a thickness 992 on top of the coagulation section 920, which is substantially uniform, and has a thickness 993 on top of the ramped surfaces 930, which is not substantially uniform as the coating 990 approaches the edges (e.g., first side 941 and second side 942). The thicknesses (e.g., thickness 992 and thickness 993) of the coating 990 regulates the current to concentrate on the blade edge 940 and restricts sparking along the blade edge 940 thereby minimizing lateral thermal damage and surgical smoke generation.

Although the structural features of coagulation section 920, ramped surface 930, and blade edge 940 of electrosurgical blade 900 are illustrated and described from the perspective of the topside of electrosurgical blade 900, it is understood that some or all of the features may also be present on the bottomside of electrosurgical blade 900. Thus, the bottomside of electrosurgical blade 900 may be a planar surface along its length or may include some or all of the features present on the topside thereof.

Any of the above-described aspects of electrosurgical blade electrodes and blades may be coated entirely or on selective portions thereof with an electrically conductive and/or non-conductive material. In certain applications, the convex/concave nature of the blade enables the use of two different coating methods. For example, in certain aspects, for concave blade geometry, a more conductive non-stick coating can be used without impacting thermal spread. Also, for example, for convex blade cross sections, a less conductive non-stick coating may be used to limit the transmission of RF energy or other electrosurgical energy into the tissue.

Any or all portions of any of the electrosurgical blade electrodes disclosed herein may be formed by any suitable techniques, e.g., machining techniques and/or metal injection molding techniques. For example, any cutouts, edging, ramping, or other surface geometry may be formed by known milling techniques, etching techniques, or other techniques not specifically described.

From the foregoing and with reference to the various figures, those skilled in the art will appreciate that certain modifications can also be made to the present disclosure without departing from the scope of the same. For example, electrosurgical blade electrode 10 may include other geometrical configurations.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. An electrosurgical blade configured to couple to an RF electrosurgical instrument, the electrosurgical blade comprising:

a proximal portion formed from a conductive material and configured to couple to a blade receptacle of an RF electrosurgical instrument;

a first section formed from the conductive material and extending distally from the proximal portion and having a first thickness;

a second section formed from the conductive material and extending distally from the first section, the second section having a second thickness less than the first thickness thereby defining a first step between the first section and the second section;

a third section formed from the conductive material and extending distally from the second section, the third section having a third thickness less than the second thickness thereby defining a second step between the second section and the third section; and a blade edge formed from the conductive material and disposed along a peripheral edge of the third section, wherein the proximal portion, the first section, the second section, the third section, and the blade edge are connected to one another to define a monolithic electrode configured to permit electrosurgical energy transmission therethrough.

2. The electrosurgical blade of claim 1, wherein the blade edge is defined by a first side, a second side, and a third side, the first side having a first length and the second side having a second length less than the first length.

3. The electrosurgical blade of claim 1, wherein the third section is configured to transmit a higher RF concentration than the second section to easily start a transection.

4. The electrosurgical blade of claim 1, wherein the first section is coated to limit RF energy transmission from the first section.

5. The electrosurgical blade of claim 1, wherein the second section is coated to limit RF energy transmission from the second section.

6. The electrosurgical blade of claim 1, wherein at least one of the first section or the second section is configured to transmit RF energy therefrom only when provided a high voltage coagulation signal.

7. The electrosurgical blade of claim 1, wherein the second step is dimensioned and configured to provide a tactile feedback to a user during dissection.

8. The electrosurgical blade of claim 1, wherein at least one of the first step or the second step is a ramped surface.

9. The electrosurgical blade of claim 1, wherein at least one of the first step or the second step is a non-ramped, perpendicular, surface.

10. An RF electrosurgical instrument comprising:

a blade receptacle; and an electrosurgical blade removably couplable to the blade receptacle, the electrosurgical blade including:

a proximal portion formed from a conductive material and configured to couple to the blade receptacle of the RF electrosurgical instrument;

a first section formed from the conductive material and extending distally from the proximal portion and having a first thickness;

a second section formed from the conductive material and extending distally from the first section, the second section having a second thickness less than the first thickness thereby defining a first step between the first section and the second section;

a third section formed from the conductive material and extending distally from the second section, the third section having a third thickness less than the second thickness thereby defining a second step between the second section and the third section; and a blade edge formed from the conductive material and disposed along a peripheral edge of the third section, wherein the proximal portion, the first section, the second section, the third section, and the blade edge are connected to one another to define a monolithic electrode configured to permit electrosurgical energy transmission through the electrosurgical blade to tissue.

11. The RF electrosurgical instrument of claim 10, wherein the blade edge is defined by a first side, a second side, and a third side, the first side having a first length and the second side having a second length less than the first length.

12. The RF electrosurgical instrument of claim 10, wherein the third section is configured to transmit a higher RF concentration than the second section to easily start a transection.

13. The RF electrosurgical instrument of claim 10, wherein the first section is coated to limit RF energy transmission from the first section.

14. The RF electrosurgical instrument of claim 10, wherein the second section is coated to limit RF energy transmission from the second section.

15. The RF electrosurgical instrument of claim 10, wherein at least one of the first section or the second section is configured to transmit RF energy therefrom only when provided a high voltage coagulation signal.

16. The RF electrosurgical instrument of claim 10, wherein the second step is dimensioned and configured to provide a tactile feedback to a user during dissection.

17. The RF electrosurgical instrument of claim 10, wherein at least one of the first step or the second step is a ramped surface.

18. The RF electrosurgical instrument of claim 10, wherein at least one of the first step or the second step is a non-ramped, perpendicular, surface.

19. An electrosurgical system comprising:

an electrosurgical generator configured to generate RF electrosurgical energy; and an RF electrosurgical instrument configured to couple to the electrosurgical generator and transmit the RF electrosurgical energy to tissue, the RF electrosurgical instrument including an electrosurgical blade including:

a proximal portion formed from a conductive material and configured to couple to a blade receptacle of the RF electrosurgical instrument;

a first section formed from the conductive material and extending distally from the proximal portion and having a first thickness;

a second section formed from the conductive material and extending distally from the first section, the second section having a second thickness less than the first thickness thereby defining a first step between the first section and the second section;

a third section formed from the conductive material and extending distally from the second section, the third section having a third thickness less than the second thickness thereby defining a second step between the second section and the third section; and a blade edge formed from the conductive material and disposed along a peripheral edge of the third section, wherein the proximal portion, the first section, the second section, the third section, and the blade edge are connected to one another to define a monolithic electrode configured to permit transmission of the RF electrosurgical energy through the electrosurgical blade to tissue.

20. The electrosurgical system of claim 19, wherein the first section is coated to limit RF energy transmission from the first section.

* * * * *